United States Patent [19]

Steiner

[11] 4,183,862
[45] Jan. 15, 1980

[54] POLYCYCLIC POLYOXYALKYLENE COMPOUNDS

[75] Inventor: Edwin C. Steiner, Midland, Mich.

[73] Assignee: The Dow Chemical Company, Midland, Mich.

[21] Appl. No.: 902,204

[22] Filed: May 2, 1978

Related U.S. Application Data

[62] Division of Ser. No. 510,872, Oct. 1, 1974, abandoned.

[51] Int. Cl.$^2$ .............................................. C07D 319/04
[52] U.S. Cl. .................................. 260/340.7; 260/338
[58] Field of Search ...................................... 260/340.7

[56] References Cited

U.S. PATENT DOCUMENTS

| | | | |
|---|---|---|---|
| 2,915,499 | 12/1959 | Wilson et al. | 260/340.7 |
| 4,113,739 | 9/1978 | Trucks et al. | 260/340.7 X |

FOREIGN PATENT DOCUMENTS 1409375  7/1965  France ..................... 260/340.7

*Primary Examiner*—Ethel G. Love
*Attorney, Agent, or Firm*—David H. Fifield; Douglas N. Deline

[57] ABSTRACT

Novel compounds of the formula

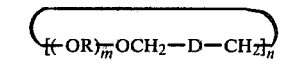

wherein —D— is a methylene group which is a member of an oxetane or a 1,3-dioxane ring, —R— is ethylene or propylene bearing from 0–6 methyl groups and m and n are lower integers. For example, a compound of the formula

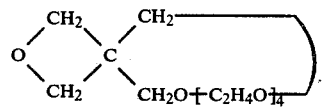

is contacted with dilute HCl to give a monomer

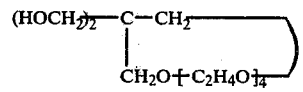

which is copolymerized with a diisocyanate to give a copolymer which removes SO$_2$ from gas streams.

13 Claims, No Drawings

POLYCYCLIC POLYOXYALKYLENE COMPOUNDS

CROSS REFERENCE TO RELATED APPLICATION

This is a division of application Ser. No. 510,872 filed Oct. 1, 1974, now abandoned.

BACKGROUND OF THE INVENTION

The novel monomers are cyclic polyoxalkylene polyethers joined by spiro linkages to one or more oxetane or 1,3-dioxane rings.

Preparation of the cyclic tetramer of ethylene oxide,

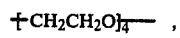

is described in British Pat. No. 785,229. Other cyclic polyethers, capable of complexing cations, have been described by Pederson in *J. Am. Chem. Soc.* 89:7017 (1967) and in U.S. Pat. No. 3,687,978. Archer, et al. in *Chem. & Ind.* 1271 (1969) describe the preparation of compounds of the formulas

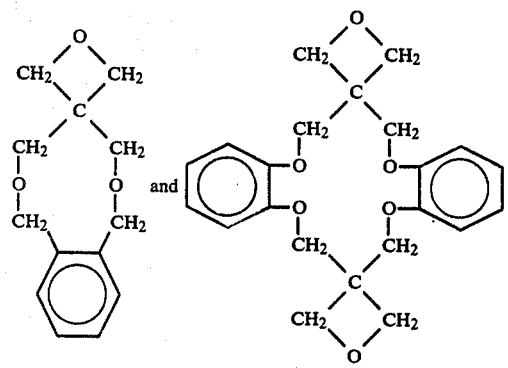

Farthing, in Chapter 5 of "High Polymers" Vol. XIII, (Interscience, 1963), describes linear polymers of the repeating units

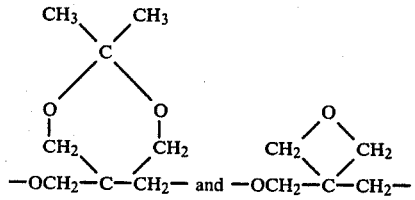

Compounds with polyoxyalkylene cyclomer functional groups have been shown to form complexes with certain alkali and alkaline earth metal cations in U.S. Pat. Nos. 3,562,295 and 3,686,225.

SUMMARY OF THE INVENTION

The invention consists of novel compounds of the formula

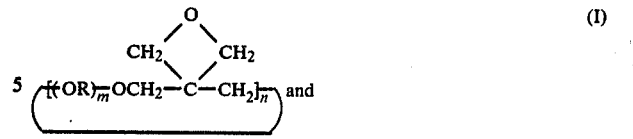

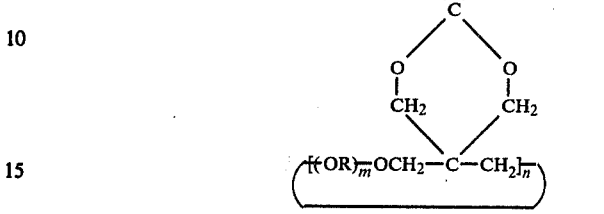

wherein m is independently, each occurrence, zero or an integer from 1 to about 10, n is an integer from 1 to 4, and —R— is an alkylene group represented by the formula

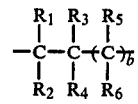

where b is zero or one, $R_1$–$R_6$ are independently hydrogen or methyl, and $R_7$ and $R_8$ are independently hydrogen or lower alkyl of 1–3 carbon atoms, provided that the product of at least one m and n is at least 2.

The compounds are useful for complexing alkali and alkaline earth metal salts and for preparing bis(hydroxymethyl) functional cyclic polyethers which may be copolymerized to form matrices capable of extracting such salts from solutions and of removing acid gases such as sulfur dioxide from gas streams.

DETAILED DESCRIPTION OF THE INVENTION

The novel compounds of the formula

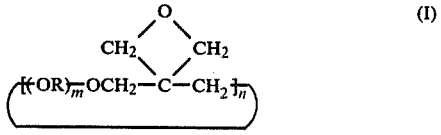

are prepared by contacting a compound of the formula

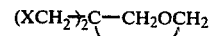

wherein X is chlorine, bromine or iodine, with about an equimolar amount of a polyoxyalkylene compound (from the corresponding polyalkylene glycol) of the formula

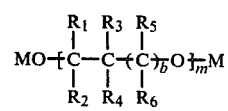

wherein m, b and $R_1$–$R_6$ are as defined above and M is an alkali metal, for example, sodium or potassium.

These reactants are contacted under an inert atmosphere suitably at about room temperature up to about 200° C., in a convenient solvent. When the reaction has gone substantially to completion, as determined by intermittent infrared spectroscopy or other suitable analytical means, remaining solvent may be removed with gentle heating under vacuum. The resulting material is a mixture of MX (alkali metal halide) and a complex of this alkali metal halide with the desired cyclic polyether (I). The mixture is extracted with several washings of boiling benzene or similar suitable aprotic solvent to dissolve the cyclic ether product, leaving the insoluble metal salts behind. The solvent is then removed and the residual liquid is distilled to obtain the pure (I).

desired cyclic polyether (II). Work up of this mixture in the manner described for (I) gives the compound (II).

Products (I) and (II) will consist of congeners wherein n is an integer from 1 to about 4 or more. These congeners are separated from one another by suitable means, for example, by fractional distillation or gel permeation chromatography. Products of formulas (I) and (II) where n is greater than unity are more prevalent when m is small, i.e., 1 or 2.

Unsymmetric products where n is greater than 1 may be produced by selecting a mixture of polyalkylene glycol salts of varying lengths, i.e., a mixture of salts of ethylene glycol and diethylene glycol will produce an unsymmetric product, for example,

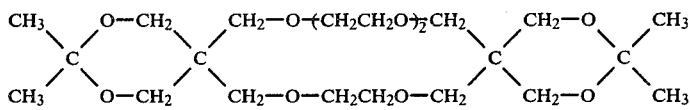

Compounds of the formula

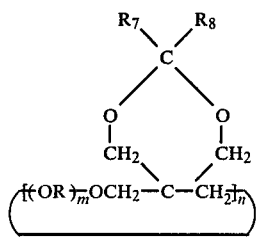

(II)

are prepared by contacting, in about equimolar amounts, a compound of the formula $(XCH_2)_2C(CH_2OH)_2$, with a lower alkyl ketone or aldehyde of the formula

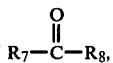

for example acetone, butanone, 2-pentanone, 3-pentanone, formaldehyde, acetaldehyde, propanal or the like, in the presence of a catalytic amount of hydrochloric acid and under dehydrating conditions. The acid is then neutralized and the resultant salt removed by successive aqueous washings and decantations of the aqueous fractions. The organic product, of the formula

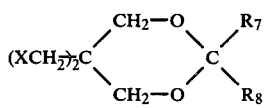

is dried over calcium chloride then contacted with about an equimolar amount of a polyoxyalkylene compound of the formula

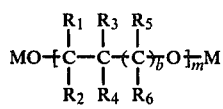

in the same manner as in the preparation of (I) above. Once again, the resulting material is a mixture of MX (alkali metal halide) and a complex of MX with the When the salt of a single polyalkylene glycol is utilized, as in preferred embodiments, the product will comprise chiefly symmetric compounds but will also comprise some unsymmetric compounds where m is zero (as it may also when a mixture of glycol salts is used) in one or more occurrences. However, the invention compounds must have at least one $(OR)_m$ moiety where m is not zero and the product of at least one m and n must be 2 or greater. In the preferred embodiments, m is the same integer, each occurrence, except positions where m is zero. These embodiments are produced where a polyalkylene glycol salt made up of m number of $(OR)$ units is selected as one reactant. Also preferred are embodiments wherein m is the same each occurrence. In the embodiments where m is the same integer each occurrence and n is greater than 1, the product of m and n will preferably be from 2 to about 12, most preferably from 2 to 6. Coproducts of varied m and n values may be separated from one another by fractional distillation or gel permeation chromatography.

The compounds preferred in the invention are those of formulas (I) and (II) wherein m is 3 to about 7, n is 1, b is zero, $R_2$ and $R_4$ and one of $R_1$ and $R_3$ are hydrogen and $R_7$ and $R_8$ are hydrogen or methyl. Most preferred are the compounds wherein —R— is ethylene and those wherein m is 3, 4 or 5. They are prepared by contacting the disodium salts of triethylene, tetraethylene or pentaethylene glycol, respectively, (i.e., where m is 3, 4, or 5) with 3,3-bis(bromomethyl) oxetane or a 5,5-bis(bromomethyl)-1,3-dioxane.

Compounds wherein —R— is 1,3-propylene may be produced from the corresponding salts of poly(trimethylene) glycols and those wherein b is zero and $R_1$ or $R_3$ is methyl may be similarly produced from the corresponding salts of polypropylene glycols (i.e., 1,2-propylene glycols).

The polyether (I) or (II) may be incorporated in a polymeric matrix by first opening the oxetane or 1,3-dioxane functional group under acid hydrolysis to form a bis(hydroxymethyl) monomer of the formula

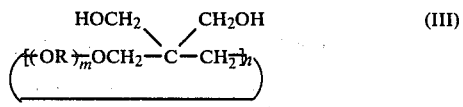

(III)

This monomer may then be copolymerized with materials such as alkylene or arylene diisocyanates, dicarboxylic acids or acids anhydrides to yield polyurethanes and polyesters which may be used to remove acid gases from gas streams and to remove alkali and alkaline earth metal salts from solutions. (I) and (II) themselves may also be used to form complexes with such salts.

SPECIFIC EMBODIMENTS OF THE INVENTION

EXAMPLE 1

Preparation of Oxetane Compounds

A solution consisting of 0.292 mole of the disodium salt of tetraethylene glycol in about 90 ml. of t.-butanol was placed in a nitrogen-purged flask equipped with mechanical stirrer and condenser. To this was added 74.43 g. (0.305 mole) of 3,3-bis(bromomethyl)oxetane which dissolved to give a clear solution. The solution was then heated to reflux temperature and maintained (about 85° C. pot temperature) for about 2 hours. Heating was discontinued and the mixture was vacuum filtered while still warm to separate a white solid, found to be sodium bromide, which had formed. Upon evaporation of the filtrate, crystals and 35 g. of a yellow oil remained. After distillation of the oil, about 12 g. of product, shown by analysis to be the compound of the formula

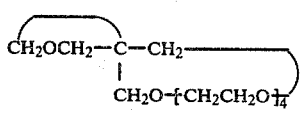

(Ia)

were recovered.

In a like manner, compounds of the formulas

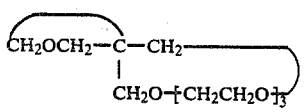

(Ib)

and

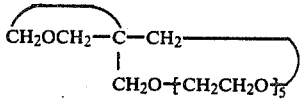

(Ic)

was prepared.

EXAMPLE 2

Poly-Oxetane Functional Cyclic Polyethers

Equivalent amounts of diethylene glycol (28.49 g.) and potassium hydroxide (35.0 g. of 85% pellets) were added to about 500 g. of t.-butanol in a 2 liter flask warmed to reflux to dissolve the KOH and then the mixture was cooled to about 45° C. at which time an equivalent amount of 3,3-bis(bromomethyl)oxetane (65.73 g.) was added. The mixture was brought slowly to reflux, at about 85°–90° C., held at that temperature for about 50 minutes and the mixture then allowed to cool.

Samples were taken of the liquid reaction mixture and vapor phase chromatography indicated that about 73% of the 3,3-bis(bromomethyl)oxetane had reacted. White potassium bromide precipitate was also observed in the reaction vessel.

Gel permeation chromatographic analysis of the liquid sample revealed the presence of at least 5 distinct products with molecular weights of about 195, 293, 380, 455 and 600 indicating the formation of the following cyclic polyethers of oxetane functionality. As can be noted, in some occurrences, m=zero:

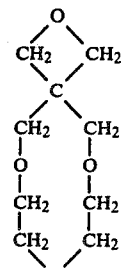

Theor. MW = 188

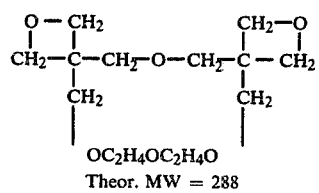

Theor. MW = 288

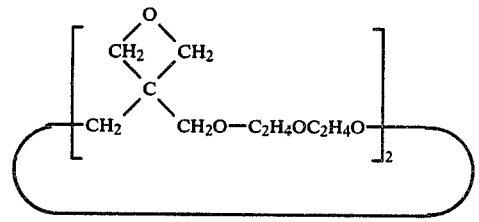

Theor. MW = 376

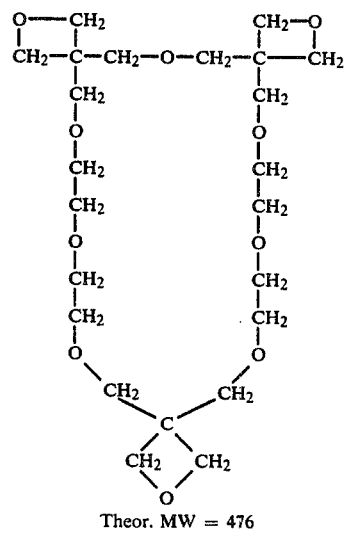

Theor. MW = 476

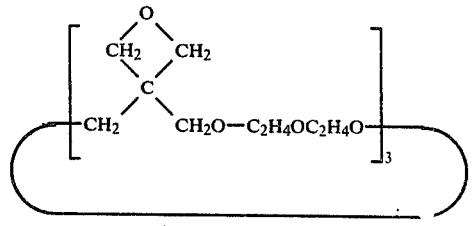

Theor. MW = 564

These compounds may be hydrolyzed with dilute HCl to form (poly) bis(hydroxymethyl) monomers which may be copolymerized with diisocyanates, dicarboxylic acids etc., to form acid gas-absorbing polymeric matrices.

EXAMPLE 3

Preparation of 1,3-Dioxane Polyethers 2,2-Dimethyl-5,5-bis(bromomethyl)-1,3-dioxane was prepared by adding 262 g. (1 mole) of 2,2-bis(bromomethyl)-1,3-propane diol to a mixture of 2 ml. (0.24 mole) of concentrated hydrochloric acid and 1500 ml. of acetone. To the mixture was added 65 g. (0.59 mole) of anhydrous calcium chloride; this mixture was then allowed to stand with occasional gentle stirring until the calcium chloride could no longer be observed to swell, about 15 hours. It was thereafter filtered and added to fresh batches of anhydrous calcium chloride, three successive times, until the calcium chloride no longer appeared to hydrate, as evidenced by lack of further swelling. After the acid in the mother liquid was neutralized with 1 g. (0.01 mole) of sodium carbonate, the liquor was filtered and evaporated to dryness. The residue was extracted with carbon tetrachloride to give a solution which was then filtered and evaporated to give 270 g. of crystalline product which by nuclear magnetic resonance spectroscopy (NMR) was identified as 2,2-dimethyl-5,5-bis(bromomethyl)-1,3-dioxane.

The disodium salt of tetraethylene glycol was prepared by adding 13.6 g. (0.59 mole) of clean sodium metal to 59.4 g. (0.31 mole) of tetraethylene glycol under nitrogen in stainless steel bomb reactor. When all the sodium had reacted, 99.4 g. (0.33 mole) of the 2,2-dimethyl-5,5-bis(bromomethyl)-1,3-dioxane was added to the stainless steel bomb in a quantity of t.-butanol solvent. The bomb was heated at about 150° C. for about 6 hours. The t.-butanol was then removed under vacuum leaving a residue of solids. These solids were extracted with boiling benzene with solid sodium bromide remaining undissolved. From the extracted liquor benzene was removed under a vacuum. The oil remaining after benzene was removed was then distilled under a vacuum of about 0.5 mm. of pressure and about 64 g. of product was recovered between about 80° C. and about 100° C. This colorless liquid product was shown by NMR, mass spectrometry and elemental analysis to be a compound represented by the formula:

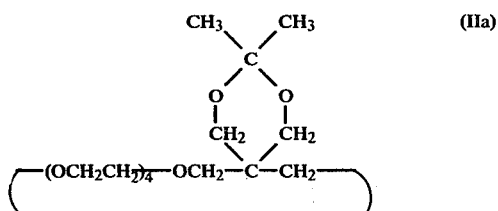
(IIa)

In a similar manner, the tri-oxyethylene analog was prepared of the formula

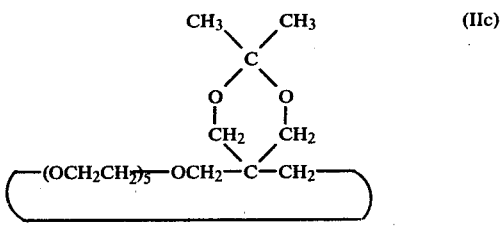
(IIb)

The cyclic penta-oxyethylene analog is likewise prepared from 2,2-dimethyl-5,5-bis-bromomethyl)-1,3-dioxane and the disodium salt of penta-ethylene glycol. The product is a compound of the formula

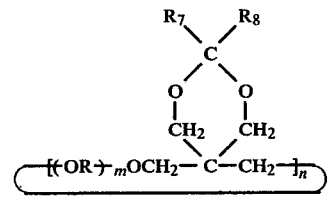
(IIc)

I claim:

1. A compound represented by the formula

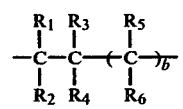

wherein m, each occurrence is independently zero or an integer from 1 to about 10, n is an integer from 1 to 4, —$R_7$ and —$R_8$ are independently hydrogen or lower alkyl, and —R— is an alkylene chain represented by the formula $$-\overset{R_1}{\underset{R_2}{C}}-\overset{R_3}{\underset{R_4}{C}}-(\overset{R_5}{\underset{R_6}{C}})_b-$$

where b is zero or one and $R_1$-$R_6$ are independently hydrogen or methyl, provided that the product of at least one m and n is at least 2.

2. A compound of claim 1 wherein n is 1, 2 or 3.
3. A compound of claim 2 wherein b is zero and $R_2$ and $R_4$ are hydrogen and one of $R_1$ and $R_3$ is hydrogen.
4. A compound of claim 3 wherein n is 1.
5. A compound of claim 4 wherein m is 3 to about 7 and $R_1$ and $R_3$ are both hydrogen.
6. A compound of claim 5 wherein $R_7$ and $R_8$ are methyl and m is 3.
7. A compound of claim 5 wherein $R_7$ and $R_8$ are methyl and m is 4.
8. A compound of claim 5 wherein $R_7$ and $R_8$ are methyl and m is 5.
9. A compound of claim 3 wherein n is 2.
10. A compound of claim 9 wherein each occurrence m is independently 0 to 2 and $R_1$ and $R_3$ are hydrogen.
11. A compound of claim 3 wherein n is 3.
12. A compound of claim 11 wherein each occurrence m is independently 0 to 2 and $R_1$ and $R_3$ are hydrogen.
13. The compound of claim 12 wherein m is 2 only.

* * * * *

UNITED STATES PATENT AND TRADEMARK OFFICE
CERTIFICATE OF CORRECTION

PATENT NO. : 4,183,862
DATED : January 15, 1980
INVENTOR(S) : Edwin C. Steiner

It is certified that error appears in the above-identified patent and that said Letters Patent are hereby corrected as shown below:

Col. 1, line 22, delete " _____ " and insert -- $\{CH_2CH_2O\}_4$ ------

Col. 1, line 26, delete "Archer, et al." and insert -- Archer et al. --

Col. 5, line 3, delete "acids anhydrides" and insert -- acid anhydrides --.

Col. 5, line 48, delete "was prepared." and insert -- were prepared. --

Signed and Sealed this

Twenty-seventh Day of May 1980

[SEAL]

Attest:

SIDNEY A. DIAMOND

Attesting Officer     Commissioner of Patents and Trademarks